United States Patent
Ellis et al.

(10) Patent No.: US 6,476,261 B2
(45) Date of Patent: Nov. 5, 2002

(54) OXIDATION PROCESS FOR THE PRODUCTION OF ALKENES AND CARBOXYLIC ACIDS

(75) Inventors: Brian Ellis, Lower Sunbury (GB); Mark Stephen Roberts, Beverly (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/964,848

(22) Filed: Sep. 28, 2001

(65) Prior Publication Data

US 2002/0099239 A1 Jul. 25, 2002

(30) Foreign Application Priority Data

Oct. 26, 2000 (GB) .............................................. 0026241

(51) Int. Cl.[7] .......................... C07B 53/00; C07C 5/327; C07C 5/373
(52) U.S. Cl. ........................................ 562/606; 585/654
(58) Field of Search .................................. 562/606, 607; 560/245; 585/650, 654

(56) References Cited

U.S. PATENT DOCUMENTS 5,162,578 A * 11/1992 McCain, Jr. et al. ..... 562/512.2
6,143,921 A * 11/2000 Karim et al. ................ 560/245

OTHER PUBLICATIONS

Derwent Abstract and translation of JP 11290684A (Machine Translation)*

* cited by examiner

*Primary Examiner*—Mukund J. Shah
*Assistant Examiner*—Zachary C. Tucker
(74) *Attorney, Agent, or Firm*—Nixon & Vanderhye

(57) ABSTRACT

A process for the oxidation of a $C_2$ to $C_4$ alkane to produce the corresponding alkene and carboxylic acid which process comprises contacting in an oxidation reaction zone, said alkane, molecular oxygen-containing gas, and optionally, at least one of the corresponding alkene and water, in the presence of at least two catalysts each active, with different selectivities, for the oxidation of the alkane to the corresponding alkene and carboxylic acid, to produce a product stream comprising said alkene, carboxylic acid and water, and in which process the molar ratio of alkene to carboxylic acid produced in said oxidation reaction zone is adjusted or maintained at a pre-determined value by controlling the relative proportions of the at least two catalysts in said oxidation reaction zone. Such an oxidation process may be used in an integrated process, such as for the manufacture of ethyl acetate or vinyl acetate.

7 Claims, 1 Drawing Sheet

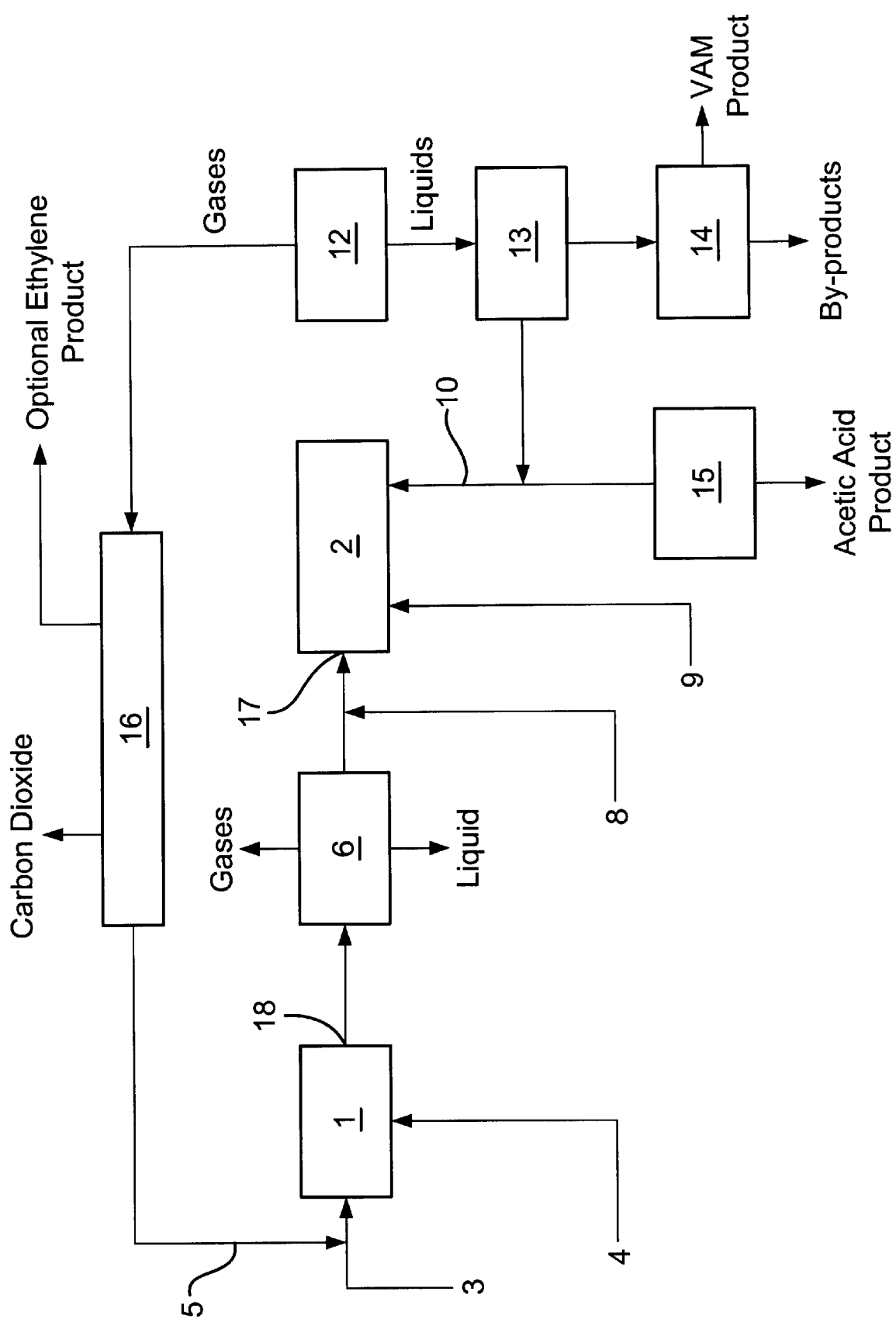

OXIDATION PROCESS FOR THE PRODUCTION OF ALKENES AND CARBOXYLIC ACIDS

The present invention relates to a process for the oxidation of a $C_2$ to $C_4$ alkane to produce the corresponding alkene and carboxylic acid and to integrated processes in which the alkene and carboxylic acid are further used as reactants.

Carboxylic acids are useful feedstocks for the production of alkenyl carboxylates. Thus, for example, acetic acid is used to manufacture vinyl acetate which is generally prepared commercially by contacting ethylene and acetic acid with molecular oxygen in the presence of a catalyst active for the production of vinyl acetate. Suitably, the catalyst may comprise palladium, an alkali metal acetate promoter and an optional co-promoter (for example, gold or cadmium) on a catalyst support. Acetic acid may be produced by the catalytic oxidation of ethylene and/or ethane.

Integrated processes for producing acetic acid and/or vinyl acetate are known in the art. EP-A-0 877 727 discloses an integrated process for the production of acetic acid and/or vinyl acetate in any pre-determined and variable proportions from a gaseous feedstock comprising ethylene and/or ethane. The integrated process comprises a first step wherein ethylene and/or ethane is catalytically oxidised in a first reaction zone to produce a first product stream comprising acetic acid, water and ethylene and optionally ethane, carbon monoxide, carbon dioxide and/or nitrogen. The acetic acid and ethylene produced in this first reaction zone are then contacted in a second reaction zone with a molecular oxygen-containing gas in the presence of a catalyst to produce a second product stream comprising vinyl acetate, water, acetic acid and optionally ethylene. No mention is made of any control of the production ratio of ethylene to acetic acid from the catalytic oxidation of ethane and/or ethylene.

Research Disclosure 2244 of 1992(June) No. 338 describes a process for the oxidation of ethane and/or ethylene to produce acetic acid in which the by-product carbon monoxide is oxidised to carbon dioxide. According to this document, the acetic acid, unreacted ethane (if present) and ethylene is passed with or without carbon dioxide and water removal, to a reactor having a suitable catalyst for the production of ethyl acetate or, with the addition of oxygen, for the production of vinyl acetate. This document is silent on the control of the ratio of ethylene to acetic acid produced in the oxidation step.

In the manufacture of vinyl acetate from ethylene and acetic acid, the molar ratio of the fresh feed ethylene to acetic acid is desirably unity or approximately unity. Thus, in an integrated process in which ethane is oxidised in an oxidation reaction zone to produce ethylene and acetic acid for use in a second reaction zone for the production of vinyl acetate, to maximise overall integrated process efficiency and also vinyl acetate output, the molar ratio of ethylene to acetic acid produced in the oxidation reaction zone, is desirably unity or approximately unity depending upon the selectivity/yield in the second reaction zone.

Thus, there remains a need for a process for the oxidation of a $C_2$ to $C_4$ alkane to produce the corresponding alkene and carboxylic acid in which the molar ratio of alkene to carboxylic acid produced is adjusted or maintained at a pre-determined value.

Accordingly, the present invention provides a process for the oxidation of a $C_2$ to $C_4$ alkane to produce the corresponding alkene and carboxylic acid which process comprises contacting in an oxidation reaction zone, said alkane, a molecular oxygen-containing gas and optionally, at least one of the corresponding alkene and water, in the presence of at least two catalysts each active, with different selectivities, for the oxidation of the alkane to the corresponding alkene and carboxylic acid, to produce a product stream comprising alkene, carboxylic acid and water, and in which process the molar ratio of alkene to carboxylic acid produced in said oxidation reaction zone is adjusted or maintained at a pre-determined value by controlling the relative proportions of the at least two catalysts in said oxidation reaction zone.

Each of the alkane, molecular oxygen-containing gas, alkene and water may be introduced into the oxidation reaction zone as fresh feed and/or recycle component.

The selectivity of a catalyst for alkene or carboxylic acid is defined as the proportion of reactant which is converted to alkene or carboxylic acid by that catalyst.

If one or more of the catalysts in the oxidation reaction zone de-activate in use and it is necessary to replace catalyst during the process, the molar ratio of alkene to carboxylic acid produced may be maintained at a constant, pre-determined value by controlling the relative proportions of the catalysts in the oxidation reaction zone. Thus, if the activity and/or selectivity of the catalysts in the oxidation reaction zone change independently during the process, this may involve replacing at least part of the catalysts in the oxidation reaction zone by introducing catalysts into the oxidation reaction zone in different proportions to the proportions of catalysts already in the oxidation reaction zone, in order to maintain the molar ratio of alkene to carboxylic acid produced. Conversely, if the catalysts in the reactor deactivate such that their individual selectivities do not change, it may be possible to maintain the molar ratio of alkene to carboxylic acid produced by using for the replacement of catalysts in the oxidation reaction zone, catalysts in the same proportions as in the oxidation reaction zone.

The present invention also provides a method of adjusting the molar ratio of alkene to carboxylic acid produced, for example in response to changes in demand or requirement in down-stream processes by controlling the relative proportions of the at least two catalyst in the oxidation reaction zone.

The process of the present invention is particularly useful when the alkene and/or carboxylic acid products are used at least in part in integrated downstream processes, for example (a) for the production of ester by reacting the carboxylic acid with the alkene or an alcohol or (b) for the production of alkenyl carboxylate by the reaction of a molecular oxygen-containing gas with the carboxylic acid and alkene. Alkene and/or carboxylic acid may be recovered from the product of the oxidation reaction zone and/or additional alkene and/or carboxylic acid may be used in the down-stream process.

In a further embodiment of the present invention, the alkene and carboxylic acid may be produced in a molar ratio suitable for use in an integrated down-stream process, for example (a) for the production of ester by reacting the carboxylic acid with the alkene or (b) for the production of alkenyl carboxylate by the reaction of a molecular oxygen-containing gas with the carboxylic acid and alkene. If alkene and/or carboxylic acid is neither separately recovered from reaction product nor separately added to the downstream process, the molar ratio of alkene to carboxylic acid produced in the oxidation reaction zone is suitably approximately 1:1, for example, 0.8:1 to 1.4:1. A different ratio may be produced if alkene and/or carboxylic acid is separately recovered from the oxidation reaction product or separately added to the down-stream process. The molar ratio of alkene to carboxylic acid may then be adjusted by controlling the relative proportions of the at least two catalysts in the oxidation reaction zone, for example to meet changes in market demand or feedstock availability. Suitably, the molar ratio of alkene to carboxylic acid produced in the oxidation reaction zone is in the range 1:10 to 10:1.

Accordingly, the present invention provides an integrated process for the production of an alkyl carboxylate which process comprises the steps:
(a) contacting in an oxidation reaction zone a $C_2$ to $C_4$ alkane, a molecular oxygen-containing gas and optionally, at least one of the corresponding alkene and water in the presence of at least two catalysts each active, with different selectivities, for the oxidation of the alkane to the corresponding alkene and carboxylic acid, to produce a product stream comprising alkene, carboxylic acid and water; and
(b) contacting in a second reaction zone at least a portion of each of said alkene and carboxylic acid produced in the first reaction zone, in the presence of at least one catalyst active for the production of alkyl carboxylate to produce said alkyl carboxylate, and in which the molar ratio of alkene to carboxylic acid produced in the oxidation reaction zone is adjusted or maintained at a pre-determined value by controlling the relative proportions of the at least two catalysts in said oxidation reaction zone.

Also, in another embodiment, the present invention provides an integrated process for the production of an alkenyl carboxylate which process comprises the steps:
(a) contacting in an oxidation reaction zone a $C_2$ to $C_4$ alkane, a molecular oxygen-containing gas and optionally, at least one of the corresponding alkene and water in the presence of at least two catalysts each active, with different selectivities, for the oxidation of the alkane to the corresponding alkene and carboxylic acid, to produce a product stream comprising alkene, carboxylic acid and water; and
(b) contacting in a second reaction zone at least a portion of each of said alkene and carboxylic acid produced in the first reaction zone and a molecular oxygen-containing gas, in the presence of at least one catalyst active for the production of alkenyl carboxylate to produce said alkenyl carboxylate,
and in which the molar ratio of alkene to carboxylic acid produced in the oxidation reaction zone is adjusted or maintained at a pre-determined value by controlling the relative proportions of the at least two catalysts in said oxidation reaction zone.

Preferably, the molar ratio of alkene: carboxylic acid produced in the oxidation reaction zone is maintained at approximately 1:1, for example, 0.8:1 to 1.4:1 for subsequent use in a second reaction zone for the production of alkyl carboxylate or alkenyl carboxylate.

In the present invention, preferably, the C2 to C4 alkane is ethane, the corresponding alkene being ethylene and the corresponding carboxylic acid being acetic acid. These products may be reacted in down-stream processes to produce ethyl acetate or, with a molecular oxygen-containing gas to produce vinyl acetate.

Typically, the oxidation reaction is performed heterogeneously with solid catalysts and the reactants in the fluid phase Catalysts active for the oxidation of alkane to alkene and carboxylic acid may comprise any suitable catalysts known in the art, for example, for the oxidation of ethane to ethylene and acetic acid as described in U.S. Pat. No. 4,596,787, EP-A-0407091, DE 19620542, WO 99/20592, DE 19630832, WO 98/47850, WO 99/51339, EP-A-0 1043064, WO 9913980, U.S. Pat. Nos. 5,300,682 and 5,300,684, the contents of which are hereby incorporated by reference.

U.S. Pat. No. 4,596,787 relates to a process for the low temperature oxydehydrogenation of ethane to ethylene using a catalyst having the empirical formula $Mo_aV_bNb_cSb_dX_e$ as therein defined, the elements being present in combination with oxygen.

EP-A-0407091 relates to process and catalyst for the production of ethylene and/or acetic acid by oxidation of ethane and/or ethylene in the presence of an oxidation catalyst comprising molybdenum, rhenium and tungsten.

DE 19620542 relates to molybdenum, palladium, rhenium based oxidation catalysts for the production of acetic acid from ethane and/or ethylene.

WO 99/20592 relates to a method of selectively producing acetic acid from ethane, ethylene or mixtures thereof and oxygen at high temperature in the presence of a catalyst having the formula $MO_aPd_bX_cY_d$ wherein X represents one or several of Cr, Mn, Nb, Ta, Ti, V, Te and W; Y represents one or several of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and a=1, b=0.0001 to 0.01, c=0.4 to 1 and d=0.005 to 1.

German patent application DE 196 30 832 A1 relates to a similar catalyst composition in which a=1, b>0, c>0 and d=0 to 2. Preferably, a=1, b=0.0001 to 0.5, c=0.1 to 1.0 and d=0 to 1.0.

WO 98/47850 relates to a process for producing acetic acid from ethane, ethylene or mixtures thereof and a catalyst having the formula $W_aX_bY_cZ_d$ in which X represents one or several of Pd, Pt, Ag and Au, Y represents one or several of V, Nb, Cr, Mn, Fe, Sn, Sb, Cu, Zn, U, Ni, and Bi and Z represents one or several of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and Te, a=1, b>0, c>0 and d is 0 to 2.

WO 99/51339 relates to a catalyst composition for the selective oxidation of ethane and/or ethylene to acetic acid which composition comprises in combination with oxygen the elements $Mo_aW_bAg_cIr_dX_eY_f$ wherein X is the elements Nb and V; Y is one or more elements selected from the group consisting of Cr, Mn, Ta, Ti, B, Al, Ga, In, Pt, Zn, Cd, Bi, Ce, Co, Rh, Cu, Au, Fe, Ru, Os, K, Rb, Cs, Mg, Ca, Sr, Ba, Zr, Hf, Ni, P, Pb, Sb, Si, Sn, Tl, U, Re and Pd; a, b, c, d, e and f represent the gram atom ratios of the elements such that $0<a\leq1$, $0\leq b<1$ and a+b=1; $0<(c+d)\leq0.1$; $0<e\leq2$; and $0\leq f\leq2$.

EP-A-1043064 relates to a catalyst composition for the oxidation of ethane to ethylene and/or acetic acid and/or for the oxidation of ethylene to acetic acid which composition comprises in combination with oxygen the elements molybdenum, vanadium, niobium and gold in the absence of palladium according to the empirical formula: $MO_aW_bAu_cV_dNb_eY_f$ wherein Y is one or more elements selected from the group consisting of: Cr, Mn, Ta, Ti, B, Al, Ga, In, Pt, Zn, Cd, Bi, Ce, Co, Rh, Ir, Cu, Ag, Fe, Ru, Os, K, Rb, Cs, Mg, Ca, Sr, Ba, Zr, Hf, Ni, P, Pb, Sb, Si, Sn, Tl, U, Re, Te, La and Pd; a, b, c, d, e and f represent the gram atom ratios of the elements such that: $0<a\leq1$; $0\leq b<1$ and a+b=1; $10-5<c\leq0.02$; $0<d\leq2$; $0<e\leq1$; and $0\leq f\leq2$.

WO 99/13980 relates to a catalyst for the selective oxidation of ethane to acetic acid of formula: $Mo_aV_bNb_cX_d$ wherein X is at least one promoter element selected from the group consisting of P, B, Hf, Te and As; a is a number ranging from about 1 to about 5; b is 1; c is a number ranging from about 0.01 to about 0.5; and d is a number ranging from greater than 0 to about 0.1.

U.S. Pat. No. 5,300,682 relates to the use of oxidation catalyst with empirical formula of $VP_aM_bO_x$ where M is one or more of Co, Cu, Re, Fe, Ni, Nb, Cr, W, U, Ta, Ti, Zr, Hf, Mn, Pt, Pd, Sn, Sb, Bi, Ce, As, Ag and Au, a is 0.5 to 3, b is 0 1 and x satisfies the valence requirements.

U.S. Pat. No. 5,300,684 relates to a fluid bed oxidation reaction using for example $Mo_{0.37}Re_{0.25}V_{0.26}Nb_{0.07}Sb_{00.03}Ca_{0.02}O_x$.

Other suitable oxidation catalysts for use in the present invention are described in WO 99/13980 which relates to the use of catalysts with elements in combination with oxygen in the relative gram atom ratios of $MO_aV_bNb_cX_d$ where X=P, B, Hf, Te or As; U.S. Pat. No. 6,030,920 which relates to the use of catalysts with elements in combination with oxygen in the relative gram atom ratios of $Mo_a V_bNb_c Pd_d$; WO 00/00284 which relates to the use of catalysts with elements in combination with oxygen in the relative gram atom ratios Of $Mo_aV_bNb_c Pd_d$ and/or $Mo_a V_bLa_cPd_d$; U.S. Pat. No. 6,087,297 which relates to the use of catalysts with elements in combination with oxygen in the relative gram atom ratios of $Mo_a V_bPd_cLa_d$; WO 00/09260 which relates to the use of catalysts with elements in combination with oxygen in the relative gram atom ratios of $Mo_a V_bLa_cPd_d$-$Nb_eX_f$ where X=Cu or Cr and e and f can be zero; WO 00/29106 and WO 00/29105 which relate to the use of catalysts with elements in combination with oxygen in the relative gram atom ratios of $Mo_a V_bGa_cPd_d Nb_eX_f$ wherein X=La, Te, Ge, Zn, Si, In or W and WO 00/38833 which relates to the use of catalysts with elements in combination with oxygen in the relative gram atom ratios of $Mo_a V_bLa_cP$-$d_dNb_eX_f$ wherein X=Al, Ga, Ge or Si, the contents of which are hereby incorporated by reference.

Solid catalysts active for the oxidation of the $C_2$ to $C_4$ alkane may be supported or unsupported. Examples of suitable supports include silica, diatomaceous earth, montmorillonite, alumina, silica alumina, zirconia, titania, silicon carbide, activated carbon and mixtures thereof.

Solid catalysts active for the oxidation of the $C_2$ to $C_4$ alkane may be used in the form of a fixed or fluidised bed.

The oxidation catalyst would be expected to oxidise at least part of any alkene fed to the oxidation reaction zone, for example to the corresponding carboxylic acid.

The molar ratio of alkene to carboxylic acid produced in the oxidation reaction zone may be adjusted or maintained at a pre-determined value by initially starting the reaction with a single catalyst and then replacing at least a part of the catalyst with at least one other catalyst having a different selectivity to alkene and carboxylic acid.

The molar ratio of alkene to carboxylic acid may be adjusted or maintained by the replacement of at least a part of the catalyst in the oxidation reaction zone with one or more catalysts with selectivities different to that of the catalyst or catalysts already present in the oxidation reaction zone. Thus, for example, the catalysts initially present in the oxidation reaction zone may be overall more selective for the production of alkene; the molar ratio of alkene to carboxylic acid produced in the oxidation reaction zone, may then be adjusted by replacement of at least a part of the catalysts already in the oxidation reaction zone with a catalyst or catalysts having a higher selectivity to carboxylic acid.

The catalyst or catalysts active for the oxidation of alkane to alkene and carboxylic acid may be replaced by methods known in the art. Thus, if operated in a fluid bed, catalyst may be removed either by entrainment or deliberately by known means and replaced by known means.

The molecular oxygen-containing gas used in the oxidation reaction zone may be air or a gas richer or poorer in molecular oxygen than air. A suitable gas may be, for example, oxygen diluted with a suitable diluent, for example nitrogen or carbon dioxide. Preferably, the molecular oxygen-containing gas is oxygen. Preferably, at least some of the molecular oxygen-containing gas is fed to the oxidation reaction zone independently from the alkane and optional alkene feeds, and any recycle streams.

The alkane and, if used, alkene fed into the oxidation reaction zone of the process of the present invention may be substantially pure or may be admixed, for example, with one or more of nitrogen, methane, carbon dioxide, carbon monoxide, hydrogen, and low levels of $C_3/C_4$ alkenes/alkanes.

Suitably, the concentration of optional alkene (as fresh feed and recycle component) is from 0 to 50 mol % inclusive of the total feed, including recycles, to the oxidation reaction zone, preferably from 1 to 20 mol %, more preferably from 1 to 15 mol %.

Suitably, the concentration of optional water (as fresh feed and recycle component) is from 0 to 50 mol % inclusive of the total feed, including recycles, to the oxidation reaction zone, preferably from 0 to 25 mol %.

When solid catalysts are used in the oxidation reaction zone alkane, optional alkene, molecular-oxygen containing gas and any recycle gases are preferably passed through the oxidation reaction zone with a residence time corresponding to a combined gas hourly space velocity (GHSV) of 500–10,000 $hr^{-1}$; the GHSV being defined as volume (calculated at STP) of gas passing through the reactor divided by the bulk volume of settled catalyst.

The oxidation reaction of the present invention may suitably be carried out at a temperature in the range from 100 to 400° C., typically in the range 140 to 350° C.

The oxidation reaction of the present invention may suitably be carried out at atmospheric or superatmospheric pressure, for example in the range from 80 to 400 psig.

Typically, alkane conversions in the range 1 to 99% may be achieved in oxidation reaction of the present invention.

Typically, oxygen conversions in the range 30 to 100% may be achieved in the oxidation reaction of the present invention.

In the oxidation reaction of the present invention, the catalyst suitably has a productivity in the range 10 to 10000 grams of carboxylic acid, such as acetic acid, per hour per kilogram of catalyst.

Depending upon the nature of any catalyst used in any downstream process, it is desirable that when used for the production of alkenyl carboxylate, such as vinyl acetate, the first gaseous product stream should have a low concentration of carbon monoxide by-product as this may have an adverse effect on some catalysts for the production of alkenyl carboxylates e.g. vinyl acetate. Thus, it is preferred to use a catalyst in the oxidation reaction zone that gives negligible carbon monoxide by-product. An additional catalyst component in the oxidation reaction zone may be used to oxidise carbon monoxide to carbon dioxide. This may be present in the oxidation catalyst or catalysts or in a secondary reaction zone.

When ethane is used as reactant for the oxidation process, the product stream comprises acetic acid, ethylene and water, and may contain ethane and oxygen, inert gas components such as argon and nitrogen and the by-products, acetaldehyde, carbon monoxide and carbon dioxide. Acetaldehyde and carbon monoxide may be converted by the molecular oxygen-containing gas to produce acetic acid and carbon dioxide respectively, either in down stream processes or, after recycling, in the oxidation reaction zone. Ethylene is present in the product stream of the oxidation reaction as unconverted reactant if ethylene is present in the feed and/or as oxidation product of the ethane reactant.

The product from the oxidation process may be fed directly or indirectly after one or more separation stages, to a second reaction zone together with optionally additional molecular oxygen-containing gas, optionally additional alkene and optionally additional carboxylic acid to produce alkenyl carboxylate, such as vinyl acetate. Carboxylic acid and/or alkene may be optionally recovered from the product of the oxidation process.

Unconverted alkane and/or alkene may be recycled together or after at least partial separation from the downstream process to the oxidation reaction zone directly or indirectly after one or more separation stages.

Catalysts known in the art for the production of alkenyl carboxylates may be used in the process of the present invention. Thus, catalyst active for the production of vinyl acetate which may be used in a second reaction zone of the present invention may comprise, for example, catalysts as described in GB 1 559 540; U.S. Pat. No. 5,185,308 and EP-A-0672453 the contents of which are hereby incorporated by reference.

GB 1 559 540 describes a catalyst active for the preparation of vinyl acetate by the reaction of ethylene, acetic acid and oxygen, the catalyst consisting essentially of: (1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per liter of catalyst, and the gold being present in an amount of from 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of vinyl acetate from ethylene, acetic acid and an oxygen containing gas, the catalyst consisting essentially of: (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

EP-A-0672453 describes palladium containing catalysts and their preparation for fluid bed vinyl acetate processes.

An advantage of using a palladium-containing catalyst is that any carbon monoxide produced in the first reaction zone will be consumed in the presence of oxygen and the palladium-containing catalyst in the second reaction zone, thereby eliminating the need for a separate carbon monoxide removal reactor.

Typically, the production of alkenyl carboxylate such as vinyl acetate in the second reaction zone is carried out heterogeneously with the reactants being present in the gas phase.

Additional alkene reactant may be fed to the second reaction zone for the production of alkenyl carboxylate as well as the alkene from the oxidation reaction zone as oxidation product and/or unconsumed alkene reactant.

Additional alkene introduced into the second reaction zone for the production of alkenyl carboxylate may be substantially pure or may be admixed, for example, with one or more of nitrogen, methane, carbon dioxide, carbon monoxide, hydrogen, and low levels of $C_3/C_4$ alkenes/alkanes.

The molecular oxygen-containing gas used in the second reaction zone for the production of alkenyl carboxylate may comprise unreacted molecular oxygen-containing gas from step (a) and/or additional molecular oxygen-containing gas.

The additional molecular oxygen-containing gas, if used, may be air or a gas richer or poorer in molecular oxygen than air. A suitable additional molecular oxygen-containing gas may be, for example, oxygen diluted with a suitable diluent, for example nitrogen or carbon dioxide. Preferably, the additional molecular oxygen-containing gas is oxygen. Preferably, at least some of the molecular oxygen-containing gas is fed independently to the second reaction zone from the alkene and carboxylic acid reactants.

At least part of the carboxylic acid fed to the second reaction zone may be liquid.

When solid catalysts are used in the second reaction zone for the production of alkenyl carboxylate, the product from the oxidation reaction zone, any additional alkene or carboxylic acid reactants, any recycle streams and molecular oxygen-containing gas are preferably passed through the second reaction zone at a combined gas hourly space velocity (GHSV) of 1000–10,000 $hr^{-1}$.

The second reaction zone for the production of alkenyl carboxylate may suitably be operated at a temperature in the range from 140 to 200° C.

The second reaction zone for the production of alkenyl carboxylate may suitably be operated at a pressure in the range 50 to 300 psig.

The second reaction zone for the production of alkenyl carboxylate may suitably be operated as either a fixed or a fluidised bed process.

Carboxylic acid conversions in the range 5 to 80% may be achieved in the second reaction zone for the production of alkenyl carboxylate.

Oxygen conversions in the range 20 to 100% may be achieved in the second reaction zone for the production of alkenyl carboxylate.

Alkene conversions in the range 5 to 100% may be achieved in the second reaction zone for the production of alkenyl carboxylate.

In the second reaction zone for the production of alkenyl carboxylate, the catalyst suitably has a productivity in the range 10 to 10000 grams of alkenyl carboxylate per hour per kg of catalyst.

When the alkane used in the process of the present invention is ethane, the product stream from the second reaction zone for the production of alkenyl carboxylate may comprise vinyl acetate, water and acetic acid and optionally also unreacted ethylene, ethane, acetaldehyde, nitrogen, argon, carbon monoxide and carbon dioxide. Such a product stream may be separated by azeotropic distillation into an overhead fraction comprising vinyl acetate and water and a base fraction comprising acetic acid and water. The base fraction may be removed from the distillation column as liquid from the bottom of the column, or as a vapour one or more stages above the bottom of the column. Prior to such a distillation step, ethylene, ethane, acetaldehyde, carbon monoxide and carbon dioxide, if any, may be removed from the second product stream, suitably as an overhead gaseous fraction from a scrubbing column, in which a liquid fraction comprising vinyl acetate, water and acetic acid is removed from the base. The ethylene and/or ethane may be recycled to step (a) and/or step (b).

Vinyl acetate is recovered from the overhead fraction, suitably for example by decantation. The recovered vinyl acetate may, if desired, be further purified in known manner.

The base fraction comprising acetic acid and water may be recycled, with or preferably without further purification, to step (b) of the process. Alternatively, acetic acid is recovered from the base fraction and may be further purified if desired, in known manner, for example by distillation.

A suitable process for the production of esters by reaction of the carboxylic acid with the alkene is described in EP-A-0926126, the contents of which are hereby incorporated by reference and which relates to an esterification process comprising reacting in an addition reaction a lower olefin with a saturated lower aliphatic mono-carboxylic acid in the vapour phase in the presence of a heteropolyacid catalyst characterised in that the reaction is carried out in a plurality of reactors set up in series such that the gases comprising the unreacted gases and products exiting from a first reactor are fed as the feed gas to a second reactor and those exiting from the second reactor are fed as feed gas to the third reactor and so on for the subsequent reactors, and an aliquot of the reactant monocarboxylic acid is introduced into the feed gas to each of the second and subsequent reactors so as to maintain the olefin to monocarboxylic acid ratio in the feed gas to each of the second and subsequent reactors within a pre-determined range.

The invention will now be illustrated by way of example only and with reference to the FIGURE and to the following examples.

The FIGURE represents in schematic block-diagram, apparatus suitable for use in the process of the present invention.

The apparatus comprises an oxidation reaction zone (1) provided with a supply of ethane and optionally ethylene (3), a supply of a molecular oxygen-containing gas (4), a supply of recycle gas comprising ethane and optionally ethylene (5) and an outlet (18) for a first product stream. Depending on the scale of the process, the oxidation reaction zone (1) may comprise either a single reactor or several reactors in parallel or series.

The apparatus also comprises a second reaction zone (2) for acetoxylation of ethylene to vinyl acetate which is provided with means (17) for conveying at least a portion of the product from the first reaction zone into the second reaction zone, a supply of molecular oxygen-containing gas (9), a supply of recycle acetic acid (10) and an optional supply or supplies of ethylene and/or acetic acid (8). Depending on the scale of the process, the second reaction zone (3) may comprise either a single reactor or several reactors in parallel or in series.

The apparatus further comprises an optional scrubber (6) for the first reaction product; a scrubber (12) for the product from the second reaction zone; means (13) for separating acetic acid from the product of the second reaction zone; vinyl acetate purfication means (14); optional acetic acid purification means (15) and one or more separation means (16) for separating carbon dioxide from recycle gases from the second reaction zone and optionally for recovery of ethylene product.

In use, the oxidation reaction zone (1) is provided with at least two catalysts each active, but with different selectivities, for the oxidation of the ethane to form acetic acid and ethylene. Suitably the oxidation catalysts are solid catalysts. Molecular oxygen-containing gas is fed to the oxidation reaction zone (1) from supply (4) through one or more inlets. A gaseous feedstock comprising ethane, and optionally ethylene is fed to the oxidation reaction zone (1) from supply (3). Recycle gas comprising ethane and ethylene is also fed to the oxidation reactor from supply (5). The molecular oxygen-containing gas, ethane and recycle gas are introduced into the oxidation reaction zone through one or more inlets separately or in partial or complete combination. Optionally, at least one of the streams fed to the oxidation reactor also comprises water.

In the oxidation reactor a first product stream is produced which comprises ethylene (as product and/or unreacted feed), acetic acid, water, optionally unconsumed molecular oxygen-containing gas and by-products such as carbon monoxide, carbon dioxide, inerts and acetaldehyde. This may optionally be passed to a scrubber (16) from which gas and liquid are removed. The gas may be recycled after separating by-products such as carbon dioxide and optionally recovering ethylene product by methods known in the art. Acetic acid may be recovered from the liquid, for example by distillation.

At least a portion of the first product stream is fed by means (17) into the second reaction zone which is provided with an acetoxylation catalyst, suitably a solid catalyst.

A molecular oxygen-containing gas is fed to the second reaction zone from supply (9). Acetic acid is fed to the second reaction zone from recycle supply (10). Optionally, additonal ethylene and/or acetic acid may be fed to the second reaction zone from supply or supplies (8). The first product stream, molecular oxygen-containing gas, recycle acetic acid and optional additional supplies of ethylene and/or acetic acid are fed into the second reaction zone through one or more inlets separately or in partial or complete combination.

In the second reaction zone the ethylene, acetic acid and molecular oxygen react to produce a second product stream comprising vinyl acetate.

The second reaction product is passed to scrubber (12) from which gas and liquid are separated. Carbon dioxide is separated from the gas and optionally ethylene product recovered, in one or more separation stages (16) by methods known in the art. The remaining ethane and/or ethylene may be recycled to the first and/or second reactors. Acetic acid is separated from the scrubber liquid and is recycled to the second reaction zone. Optionally, acetic acid product may be recovered from the recycle stream by means (15), for example by distillation. Vinyl acetate product is recovered from the scrubber liquid by means (14), for example by distillation.

In use, if one or more of the catalysts in the oxidation reaction zone de-activate and it is necessary to replace catalyst during the process, the molar ratio of ethylene to acetic acid produced may be maintained at a constant, pre-determined value by controlling the relative proportions of the catalysts in the oxidation reaction zone. Thus, if the activity and/or selectivity of the catalysts in the oxidation reaction zone change independently during the process, this may involve replacing at least part of the catalysts in the oxidation reaction zone by introducing catalysts into the oxidation reaction zone in different proportions to the proportions of catalysts in the oxidation reaction zone, in order to maintain the molar ratio of ethylene to acetic acid produced. Conversely, if the catalysts in the reactor deactivate such that their individual selectivities do not change, it may be possible to maintain the molar ratio of ethylene to acetic acid produced by using for the replacement of catalysts in the oxidation reaction zone, catalysts in the same proportions as in the oxidation reaction zone.

Preferably, the molar ratio of ethylene: acetic acid produced in the oxidation reaction zone is maintained at approximately 1:1, for example, 0.8:1 to 1.4:1 for subsequent use in the second reaction zone for the production of vinyl acetate. A different ratio may be maintained if ethylene and/or acetic acid is separately recovered from the oxidation reaction product or separately added to the second reaction zone for the production of vinyl acetate. The molar ratio of ethylene to acetic acid may then be adjusted by controlling the relative proportions of the at least two catalysts in the oxidation reaction zone, for example to meet changes in market demand or feedstock availability.

Preparation of Catalysts Active for Ethane Oxidation (catalyst A)

A solution was prepared by dissolving 17.66 g ammonium molybdate, 2.92 g ammonium vanadate, 3.24 g niobium chloride and 2.70 g oxalic acid in 400 ml water heated to 70° C. with stirring. To this solution was added 24.6 mg of ammonium tetrachloroaurate and 15.5 mg of palladium acetate. After 15 minutes, the solution water was heated to boiling point followed by evaporation to dryness over 2 hours. The resulting catalyst cake was ground and then calcined in static air in an oven at 400° C. for 5 hours. The nominal empirical formula of the catalyst was $Mo_{1.00}V_{0.25}Nb_{0.12}Au_{0.0007}Pd_{0.0008}O_x$ Preparation of Catalysts B–E The method of preparation of catalyst A was repeated except that the gold-palladium component was replaced by a component selected from the group consisting of gold, copper, silver and phosphorus as shown in Table I below to give a range of catalyst compositions based upon a base composition having empirical formula $Mo_{1.00}V_{0.25}Nb_{0.125}O_x$ but with different promoters.

TABLE I

| Catalyst | Component Precursor | Amount of component precursor salt (g) | Nominal catalyst empirical formula |
|---|---|---|---|
| Catalyst B | Ammonium tetrachloroaurate | 0.428 g | $Mo_{1.00}V_{0.25}Nb_{0.125}Au_{0.014}O_x$ |
| Catalyst C | Copper acetate | 0.280 g | $Mo_{1.00}V_{0.25}Nb_{0.125}Cu_{0.014}O_x$ |
| Catalyst D | Silver acetate | 0.111 g | $Mo_{1.00}V_{0.25}Nb_{0.125}Ag_{0.007}O_x$ |
| Catalyst E | Ammonium hydrogen phosphate | 0.090 g | $Mo_{1.00}V_{0.25}Nb_{0.125}P_{0.0025}O_x$ |

Ethane Oxidation Reaction Method for Catalysts A–E

Typically, 5 ml of a powdered catalyst A–E was mixed with 15 ml of glass beads of diameter 0.4 mm to form a diluted catalyst bed of 20 ml in volume. The diluted catalyst was then loaded into a fixed bed reactor made of Hastelloy of dimensions 12 mm internal diameter and length 40 cm. The catalyst was maintained in position in the centre of the reactor using quartz wall plugs together with inert packing material above and below the catalyst bed. The apparatus was then pressure-tested at 20 bar with helium to check for leaks. The catalyst was then activated by heating to 220° C. at 5° C./min in helium at 21 bar for 4 hours, to ensure full decomposition of catalyst precursors.

The required flows of ethane, 20% oxygen in helium and water were then introduced to the reactor, to ensure the required inlet composition. This composition was 42% v/v ethane, 6.7% oxygen, 25% v/v water and balance helium. The total feed flow rate was maintained at a level to ensure a feed GHSV of 2000–9000/h. After equilibrating for 60 minutes, gas samples were taken from the outlet stream to a GC system (model Unicam 4400) to quantify ethane, ethylene, oxygen and helium.

The setpoint temperature of the reactor was increased until 50–75% oxygen conversion was achieved, as indicated by the calculated level of oxygen in the outlet stream. Following a further equilibration period of 60 minutes, the catalyst was then evaluated under steady state conditions for a period of typically 4–5 hours. Exit gas volume was measured over the run period by a water-gas meter. Liquid products were collected and weighed after the run period. Composition of gas and liquid products was measured using GC analysis (Unicam 4400 and 4200 fitted with TCD and FID detectors respectively).

From analysis of the feed and product flow rates and compositions the following parameters were calculated:

ethane conversion=(inlet mol ethane—outlet mol ethane)/inlet mol ethane * 100 oxygen conversion=(inlet mol oxygen—outlet mol oxygen)/inlet mol oxygen * 100 selectivity to acetic acid (C-mol %)=(outlet mol acetic acid * 2)/(mol ethane converted * 2) * 100 selectivity to ethylene (C-mol %)=(outlet mol ethylene—inlet mol ethylene)* 2/(mol ethane converted * 2) * 100 selectivity to CO (C-mol %)=(outlet mol CO)/(mol ethane converted * 2) * 100 selectivity to $CO_2$ (C-mol %)=(outlet mol $CO_2$)/(mol ethane converted * 2) * 100 ethylene/AcOH ratio=(outlet mol ethylene—inlet ethylene mol)/(mol acetic acid) * 100.

STY (space time yield) %=(g acetic acid)/kg catalyst bed/hour

Typically, mass balance and carbon balance for a reaction was found to be 100+/−5%.

EXAMPLES 1 to 5

The catalysts A–E were employed in the general reaction method above. The results are shown in Table II below.

TABLE II

Oxidation reactions with base catalyst composition having empirical formula $Mo_{1.00}V_{0.25}Nb_{0.125}O_x$ and with promoter components as in Table II

| Catalyst | Catalyst Component | Ethane conversion % | Selectivity to ethylene % | Selectivity to acetic acid % | Selectivity to carbon oxides, COx % | Molar ratio Ethylene:acetic acid | STY to acetic acid g/l-cat/h |
|---|---|---|---|---|---|---|---|
| A | Au—Pd | 6.8 | 23.2 | 63.8 | 12.7 | 0.36:1 | 179 |
| B | Au | 10.0 | 34.6 | 54.9 | 8.8 | 0.63:1 | 203 |
| C | Cu | 8.0 | 35.8 | 55.6 | 8.3 | 0.64:1 | 158 |

TABLE II-continued

Oxidation reactions with base catalyst composition having empirical formula
$Mo_{1.00}V_{0.25}Nb_{0.125}O_x$ and with promoter components as in Table II

| Catalyst | Catalyst Component | Ethane conversion % | Selectivity to ethylene % | Selectivity to acetic acid % | Selectivity to carbon oxides, COx % | Molar ratio Ethylene:acetic acid | STY to acetic acid g/l-cat/h |
|---|---|---|---|---|---|---|---|
| D | Ag | 4.0 | 39.6 | 53.0 | 7.3 | 0.75:1 | 118 |
| E | P | 12.2 | 56.9 | 28.3 | 9.6 | 2.01:1 | 130 |

The results of the above Examples show that the selectivities to ethylene and acetic acid of the different catalysts under the same reaction conditions are different. Therefore, if at least two of the catalysts are used in an oxidation reaction zone according to the process of the present invention, the molar ratio of ethylene to acetic acid can be adjusted or maintained at a predetermined value by controlling the relative proportions of the at least two catalysts in the oxidation reaction zone.

Preparation of Catalysts F–N Active for Ethane Oxidation

Catalyst F

A solution 'A' was prepared by dissolving 107.70 g of ammonium molybdate in 300 ml of distilled water heated to 70° C. with stirring. A solution 'B' was prepared by dissolving 30.41 g of ammonium vanadate in 300 ml of distilled water heated to 70° C. with stirring. A solution 'C' was prepared by dissolving 18.91 g of niobium chloride 11.96 g of antimony acetate, 2.76 g of potassium carbonate and 15.75 g of oxalic acid in 300 ml of distilled water heated to 70° C. with stirring. Each of the solutions A, B and C was allowed to stand for 15 minutes to allow maximum solubilisation of the reaction components. Solution C was then rapidly added to solution B with stirring at 70° C. The solution B/C was stirred for 15 minutes at 70° C. and then added rapidly to solution A. After 15 minutes the solution A/B/C was heated to boiling point followed by evaporation to dryness over 2.5 hours. The resulting dry catalyst cake was then transferred to an oven for further drying at 120° C. for 2 hours. After drying, the catalyst cake was ground to a fine powder. The resulting powder was then sieved through a 0.2 mm mesh sieve. The sieved powder catalyst was then calcined in static air in an oven at 400° C. for 4 hours. The nominal empirical formula of the catalyst was:

$Mo_{1.000}V_{0.426}Nb_{0.115}Sb_{0.066}K_{0.033}O_x$

Catalyst G

A solution 'A' was prepared by dissolving 43.2 g of ammonium molybdate in 100 ml of distilled water heated to 70° C. with stirring. A solution 'B' was prepared by dissolving 11.4 g of ammonium vanadate in 120 ml of distilled water heated to 70° C. with stirring. A solution 'C' was prepared by dissolving 16.18 g of ammonium niobium oxalate and 2.5 g of oxalic acid in 100 ml of distilled water heated to 70° C. with stirring. Each of the solutions A, B and C was allowed to stand for 15 minutes to allow maximum solubilisation of the reaction components. Solution C was then rapidly added to solution B with stirring at 70° C. After stirring solution B/C for 15 minutes at 70° C., solution A was added rapidly to it. After 15 minutes a solution 'D' (2.57 g of ammonium phosphate dissolved in 20 ml water) was added with stirring. The A/B/C/D solution was heated to boiling point followed by evaporation to dryness over 1.5 hours. The resulting dry catalyst cake was then transferred to an oven for further drying at 120° C. for 16 hours. After drying, the catalyst cake was ground to a fine powder. The resulting powder was then sieved through a 0.2 mm mesh sieve. The sieved powder catalyst was then calcined in static air in an oven at 350° C. for 4 hours. The nominal empirical formula of the catalyst was:

$Mo_{1.000}V_{0.400}Nb_{0.128}P_{0.080}O_x$

Catalyst H

A solution 'A' was prepared by dissolving 22.935 g of ammonium molybdate and 0.0357 g of ammonium gold chloride in 100 ml of distilled water heated to 70° C. with stirring. A solution 'B' was prepared by dissolving 6.434 g of ammonium vanadate in 150 ml of distilled water heated to 70° C. with stirring. A solution 'C' was prepared by dissolving 7.785 g of ammonium niobium oxalate in 100 ml of distilled water heated to 70° C. with stirring. Each of the solutions A, B and C was allowed to stand for 15 minutes to allow maximum solubilisation of the reaction components. Solution C was then rapidly added to solution B with stirring at 70° C. The solution B/C was then stirred for 15 minutes at 70° C. and then added rapidly to solution A. After 15 minutes the A/B/C solution was heated to boiling point followed by evaporation to dryness over 1.5 hours. The resulting dry catalyst cake was then transferred to an oven for further drying at 120° C. for 2 hours. After drying, the catalyst cake was ground to a fine powder. The resulting powder was then sieved through a 0.2 mm mesh sieve. The sieved powder catalyst was then calcined in static air in an oven at 400° C. for 4 hours. The nominal empirical formula of the catalyst was:

$Mo_{1.000}V_{0.423}Nb_{0.115}Au_{0.008}O_x$

Catalyst I

A solution 'A' was prepared by dissolving 20.97 g of ammonium molybdate and 0.0337 g of palladium acetate in 100 ml of distilled water heated to 70° C. with stirring. A solution 'B' was prepared by dissolving 7.749 g of ammonium vanadate in 200 ml of distilled water heated to 70° C. with stirring. A solution 'C' was prepared by dissolving 5.626 g of ammonium niobium oxalate, 0.598 g of antimony acetate and 0.472 g of calcium nitrate in 200 ml of distilled water heated to 70° C. with stirring. Each of the solutions A, B and C was allowed to stand for 15 minutes to allow maximum solubilisation of the reaction components. Solution C was then rapidly added to solution B with stirring at 70° C. After stirring the solution B/C for 15 minutes at 70° C., solution A was rapidly added to it. After 15 minutes the A/B/C solution was heated to boiling point followed by evaporation to dryness over 1.5 hours. The resulting dry catalyst cake was then transferred to an oven for further drying at 120° C. for 2 hours. After drying, the catalyst cake was ground to a fine powder. The resulting powder was then sieved through a 0.2 mm mesh sieve. The sieved powder catalyst was then calcined in static air in an oven at 350° C. for 4 hours. The nominal empirical formula of the catalyst was:

$Mo_{1.000}V_{0.5577}Nb_{0.0913}Sb_{0.0168}Ca_{0.0168}Pd_{0.0013}O_x$

Catalyst J

A solution 'A' was prepared by dissolving 15.491 g of ammonium molybdate in 100 ml of distilled water heated to 80° C. with stirring. A solution 'B' was prepared by dissolving 5.594 g of ammonium vanadate and 6.00 g of oxalic acid in 150 ml of distilled water heated to 80° C. with stirring. Each of the solutions A and B was allowed to stand for 15 minutes to allow maximum solubilisation of the reaction components. Solution A was then rapidly added to solution B with stirring at 80° C. After stirring the solution A/B for 15 minutes at 80° C., 0.0053 g of palladium acetate and 0.0004 g of lanthanum nitrate were added with stirring. After 15 minutes the solution was heated to boiling point followed by evaporation to dryness over 1.5 hours. The resulting dry catalyst cake was then transferred to an oven for further drying at 120° C. for 2 hours. After drying, the catalyst cake was ground to a fine powder. The resulting powder was then sieved through a 0.2 mm mesh sieve. The sieved powder catalyst was then calcined in static air in an oven at 350° C. for 4 hours. The nominal empirical formula of the catalyst was:

$Mo_{1.000}V_{0.584}Pd_{0.000267}La_{0.00001}O_x$

Catalysts K–N

Catalysts K–N were prepared by grinding together catalysts H (based on Au) and I (based on Pd) in different proportions. The relative quantities of catalysts H and I used to prepare each of catalysts K–N are shown in Table III.

TABLE III

| Catalyst | Weight % catalyst H | Weight % catalyst I |
|---|---|---|
| Catalyst K | 97.6 | 2.4 |
| Catalyst L | 95.2 | 4.8 |
| Catalyst M | 92.3 | 7.7 |
| Catalyst N | 75.0 | 25.0 |

Ethane Oxidation Reaction Method for catalysts F–N.

Typically, 5 ml of a powdered catalyst F–N was mixed with 15 ml of glass beads of diameter 0.4 mm to form a diluted catalyst bed of 20 ml in volume. The diluted catalyst was then loaded into a fixed bed reactor made of Hastelloy of dimensions 12 mm internal diameter and length 40 cm. The catalyst was maintained in position in the centre of the reactor using quartz wall plugs together with inert packing material above and below the catalyst bed. The apparatus was then pressure-tested at 20 bar with helium to check for leaks. The catalyst was then activated by heating to 220° C. at 5° C./min in helium at 16 bar for 1 hour, to ensure full decomposition of catalyst precursors.

The required flows of ethane, 20% oxygen in helium and water were then introduced to the reactor, to ensure the required inlet composition. This composition was 52% v/v ethane, 6.7% oxygen, 10% v/v ethylene, 5% v/v water and balance helium. The total feed flow rate was maintained at a level to ensure a feed GHSV of 2000–9000/h, in particular 3200/h. After equilibrating for 60 minutes, gas samples were taken from the outlet stream to a GC system (model Unicam 4400) to quantify ethane, ethylene, oxygen and helium.

The setpoint temperature of the reactor was increased to 293° C., to achieve a similar reactor temperature of 299–301° C. for each of catalysts F–J, in order to facilitate direct comparison. Following a further equilibration period of 60 minutes, liquid product collection was commenced and continued for a period of typically 18 hours. During the run period, the effluent gas composition was measured using GC analysis (ProGC, Unicam). Exit gas volume was measured over the run period by a water-gas meter. The liquid products collected over the run period were recovered and weighed. The composition of the liquid products was measured using GC analysis (Unicam 4400 and 4200 fitted with TCD and FID detectors respectively).

From analysis of the feed and product flow rates and compositions, feed conversions, product selectivities, space time yield (STY) and the molar ratio of ethylene to acetic acid were calculated using the equations as given above under ethane oxidation reaction method for catalysts A–E.

EXAMPLES 6 to 10

The catalysts F to J were employed in the general reaction method for catalysts F to N above. The results are shown in Table IV below.

TABLE IV

| Catalyst | Catalyst Component | Ethane conversion % | Selectivity to ethylene % | Selectivity to acetic acid % | Selectivity to carbon oxides, CO$x$ % | Molar ratio Ethylene:acetic acid | STY to acetic acid g/kg-cat/h |
|---|---|---|---|---|---|---|---|
| F | Mo—V—Nb—Sb—K | 4.5 | 12.9 | 59.3 | 27.8 | 0.22:1 | 97 |
| G | Mo—V—Nb—P | 4.6 | 37.4 | 47.5 | 15.1 | 0.79:1 | 81 |
| H | Mo—V—Nb—Au | 11.8 | 46.5 | 40.1 | 13.3 | 1.16:1 | 175 |
| I | Mo—V—Nb—Sb—Ca—Pd | 4.7 | N/A[a] | 76.0 | 24.0 | −0.54:1[b] | 216 |
| J | Mo—V—Pd—La | 4.6 | N/A[a] | 71.4 | 28.7 | −0.55:1[b] | 201 |

[a] A value for ethylene selectivity could not be calculated because the catalyst was a net ethylene consumer
[b] The negative value for the ethylene/acetic acid molar ratio indicates that the catalyst is a net ethylene consumer rather than a producer.

The results of Examples 6–10 demonstrate that the selectivities to ethylene and acetic acid of the different catalysts under the same reaction conditions are different and thus the molar ratio of ethylene to acetic acid could be adjusted or maintained at a pre-determined value by using two different catalysts in the oxidation reaction zone in controlled proportions.

EXAMPLES 11–14

The mixed catalysts K to N were employed in the general reaction method for catalysts F to N above. The results are shown in Table V below.

TABLE V

| Catalyst | Catalyst H and I proportions wt % | Ethane conversion % | Selectivity to ethylene % | Selectivity to acetic acid % | Selectivity to carbon oxides, COx % | Molar ratio Ethylene:acetic acid | STY to acetic acid g/kg-cat/h |
|---|---|---|---|---|---|---|---|
| H | Mo—V—Nb—Au | 11.8 | 46.5 | 40.1 | 13.3 | 1.16:1 | 175 |
| K | 97.6 H—2.4 I | 8.5 | 36.5 | 47.5 | 16.0 | 0.77:1 | 149 |
| L | 95.2 H—4.8 I | 7.0 | 8.2 | 66.4 | 25.4 | 0.12:1 | 172 |
| M | 92.3 H—7.7 I | 6.2 | N/A[a] | 73.7 | 26.3 | −0.08:1[b] | 179 |
| N | 75.0 H—25.0 I | 5.0 | N/A[a] | 75.8 | 24.2 | −0.41:1[b] | 203 |
| I | Mo—V—Nb—Sb—Ca—Pd | 4.7 | N/A[a] | 76.0 | 24.0 | −0.54:1[b] | 216 |

[a] and [b] as specified for Table IV above.

Inspection of Table V clearly illustrates that by controlling the relative proportions of the different catalysts H and I in the oxidation reaction zone the molar ratio of ethylene to acetic acid can be adjusted to a pre-determined value.

What is claimed is:

1. A process for the oxidation of a $C_2$ to $C_4$ alkane to produce the corresponding alkene and carboxylic acid which process comprises contacting in an oxidation reaction zone, said alkane, molecular oxygen-containing gas, and optionally, at least one of the corresponding alkene and water, in the presence of at least two catalysts each active, with different selectivities, for the oxidation of the alkane to the corresponding alkene and carboxylic acid, to produce a product stream comprising said alkene, carboxylic acid and water, and in which process the molar ratio of alkene to carboxylic acid produced in said oxidation reaction zone is adjusted or maintained at a pre-determined value by controlling the relative proportions of the at least two catalysts in said oxidation reaction zone.

2. A process as claimed in claim 1 in which the molar ratio of alkene to carboxylic acid produced in the oxidation reaction zone is in the range of 1:10 to 10:1.

3. A process according to claim 2 wherein the molar ratio of alkene to carboxylic acid produced in the oxidation reaction zone is in the range of 0.8:1 to 1.4:1.

4. A process as claimed in claim 1 in which the alkane is ethane, the corresponding alkene being ethylene and the corresponding carboxylic acid being acetic acid.

5. A process according to claim 1 wherein the molar ratio of alkene to carboxylic acid produced in the oxidation reaction zone is adjusted or maintained at a pre-determined value by replacing at least part of one or both of the catalysts present in the oxidation reaction zone with one or more catalysts having selectivities to alkene and/or carboxylic acid different than those of the catalyst(s) previously present in the oxidation reaction zone.

6. A process according to claim 1 in which at least one of the at least two catalysts in the oxidation reaction zone comprises molybdenum.

7. A process according to claim 6 wherein each catalyst in the oxidation reaction zone comprises molybdenum.

* * * * *